United States Patent [19]

Patel

[11] Patent Number: 4,798,725

[45] Date of Patent: Jan. 17, 1989

[54] SUSTAINED RELEASE CAPSULE

[75] Inventor: Vikram S. Patel, Norwich, N.Y.

[73] Assignee: Norwich Eaton Pharmaceuticals, Inc., Norwich, N.Y.

[21] Appl. No.: 874,732

[22] Filed: Jun. 16, 1986

[51] Int. Cl.$^4$ .............................................. A61K 9/64
[52] U.S. Cl. .................................... 424/456; 424/457; 424/458
[58] Field of Search ................ 424/14, 16, 21, 80, 424/452, 451, 456, 457, 463, 489

[56] References Cited

U.S. PATENT DOCUMENTS

| | | | |
|---|---|---|---|
| 2,610,181 | 9/1952 | Hayes | 548/311 |
| 3,401,221 | 9/1968 | Borgmann et al. | 514/390 |
| 3,427,378 | 2/1969 | Henderson et al. | 424/14 |
| 3,444,290 | 5/1969 | Wai | 424/4 |
| 3,458,622 | 7/1969 | Hill | 424/19 |
| 3,634,584 | 1/1972 | Poole | 424/22 |
| 4,016,254 | 4/1977 | Seager | 424/80 |
| 4,122,157 | 10/1978 | Huber | 424/21 |
| 4,126,672 | 11/1978 | Sheth et al. | 424/22 |
| 4,152,444 | 5/1979 | Vischer et al. | 514/183 |
| 4,252,786 | 2/1981 | Weiss et al. | 424/19 |
| 4,343,789 | 8/1982 | Kawata et al. | 424/78 |
| 4,370,313 | 1/1983 | Davies | 424/32 |
| 4,404,183 | 9/1983 | Kawata et al. | 424/19 |
| 4,610,875 | 9/1986 | Panoz et al. | 424/80 |

FOREIGN PATENT DOCUMENTS 1204580  9/1970  United Kingdom .................. 424/37

OTHER PUBLICATIONS

El Egakey, M. A., "In Vitro and in Vivo Release Studies of Nitrofurantoin from Coated Crystals", *Acta Pharmaceutica Technologica*, vol. 28, No. 4 (1982), pp. 267–271.

Primary Examiner—Thurman K. Page
Assistant Examiner—L. R. Horne
Attorney, Agent, or Firm—Milton B. Graff, IV; David L. Suter; Jack D. Schaeffer

[57] ABSTRACT

The invention involves a sustained release pharmaceutical capsule for oral administration comprising, in a capsule shell, a particulate mixture comprising an active drug ingredient which is a weak acid, neutral, or a weak base, polyvinylpyrrolidone, and carboxyvinylpolymer.

14 Claims, No Drawings

SUSTAINED RELEASE CAPSULE

TECHNICAL FIELD

This invention is concerned with novel pharmaceutical dosage unit forms in which a sustained release of the active drug ingredient is achieved. More particularly, it is concerned with sustained release and combination sustained release/rapid release capsules comprising an active drug ingredient, polyvinylpyrrolidone, and carboxyvinylpolymer.

BACKGROUND OF THE INVENTION

Sustained release pharmaceutical dosage unit forms are well-known, and carboxyvinylpolymer and polyvinylpyrrolidone are substituents known to be used in a variety of sustained release pharmaceutical dosage unit forms.

U.S. Pat. No. 3,458,622 issued to Hill on July 29, 1969, discloses controlled release tablets which are produced by blending a medicament with polyvinylpyrrolidone and carboxyvinylpolymer, granulating, drying, and compressing into tablets. The ratio of polyvinylpyrrolidone:carboxyvinylpolymer in these controlled release tablets is from about 1:10 to 10:1. Hill discloses that "(w)hen the resulting tablet is placed in water or gastric fluid, the two polymeric substances react to form a complex of low solubility which is gumlike in consistency and . . . retards the diffusion of the active material from the tablet." Hill also notes that there is a rapid release of some of the medicament because " . . . the active material near the surface is allowed to diffuse out of the tablet fairly rapidly. As the moisture penetration becomes deeper, the restraining matrix becomes thicker and reduces the diffusion rate of the active substance. When the tablet is transferred to intestinal fluid, . . . the entire matrix is then eroded," thus providing the sustained release of the active substance trapped therein. (See column 1, lines 38-52.)

U.S. Pat. No. 3,634,584 issued to Poole on Jan. 11, 1972, discloses a controlled release tablet in which the controlled release is achieved by combining carboxyvinylpolymer and polyethyleneglycol. Poole achieves a combination of rapid release and sustained release by producing a two-layer tablet, one layer containing the controlled release formulation and the other layer containing a formulation of the active material which disintegrates rapidly to make the active material contained therein quickly available.

El Egakey, M. A., "In vitro and in vivo Release Studies of Nitrofurantoin from Coated Crystals", *Acta Pharmaceutica Technologica*, Vol. 28, No. 4 (1982), pp. 267-271, discloses pharmaceutical dosage forms in which crystals of nitrofurantoin were coated with a mixture of polyvinylpyrrolidone and carboxyvinylpolymer. Sustained release of this dosage form is achieved by having different coated crystal particles release their entrapped nitrofurantoin at different times. The coated crystal particles can be made into a capsule dosage form by filling them into a hard gelatin capsule shell, or can be made into a tablet by compressing them together in a standard tableting operation.

U.S. Pat. Nos. 4,343,789 and 4,404,183 issued to Kawata, Aruga, Ohmura, Sonobe, Yoneya & Sone on Aug. 10, 1982 and Sept. 12, 1983, respectively, disclose sustained release dosage forms made by dissolving an active material with a polymeric material and then drying the solution to form an amorphous mixture of the active material and polymer. The amorphous material is broken into small particles which are then filled into hard gelatin capsule shells. Either carboxyvinylpolymer or polyvinylpyrrolidone are disclosed as polymeric materials which can be used to produce these sustained release capsules.

U.S. Pat. No. 4,126,672 issued to Sheth & Tossounian on Nov. 21, 1978, discloses sustained release pharmaceutical capsules which are powder mixtures of medicaments with a hydrocolloid or mixture of hydrocolloids. Carboxyvinylpolymer is disclosed as one of the hydrocolloids useful in achieving such sustained release capsules. *Sheth & Tossounian* discloses that "(u)pon oral ingestion of the sustained release capsules . . . , the capsule shell dissolves leaving the formulation in contact with gastric fluid. Upon contact with gastric fluid, the outermost hydrophyllic colloid hydrates to form an outside barrier which substantially retains the shape of the capsule and therefore acts to prevent the mass from disintegrating." (See column 2, lines 38-44.) These hydrated powder masses swell in gastric fluid such that "they have a bulk density . . . less than one and therefore are buoyant in gastric fluid and thus are retained in a buoyant state in the stomach until substantially all the medicament is released therefrom." (See column 2, lines 10-14.) "(A)fter substantially all the medicaments therein are released, the gelatinous mass disperses." (See column 2, lines 35-37.)

SUMMARY OF THE INVENTION

It is an object of the present invention to provide novel sustained release pharmaceutical capsules for oral administration of an active drug ingredient.

It is a further object of the present invention to provide a process for producing such sustained release pharmaceutical capsules.

It is also an object of the present invention to provide a combination sustained release/rapid release pharmaceutical capsule for oral administration of an active drug ingredient.

It is a further object of the present invention to provide a process for producing such combination sustained release/rapid release pharmaceutical capsules.

The present invention involves a sustained release pharmaceutical capsule for oral administration comprising a particulate mixture in a capsule shell which is soluble in a gastrointestinal juice, said particulate mixture comprising:

(a) from about 0.01% to about 90% of an active drug ingredient which is a weak acid, neutral, or a weak base;

(b) from about 5% to about 96% of polyvinylpyrrolidone; and (c) from about 4% to about 40% of carboxyvinylpolymer;

wherein said polyvinylpyrrolidone and said carboxyvinylpolymer occur substantially entirely in separate particles of said particulate mixture.

DETAILED DESCRIPTION OF THE INVENTION

The present invention relates to sustained release pharmaceutical capsules for oral administration in which a particulate mixture is contained in a capsule shell which is soluble in a gastrointestinal juice. "Particulate mixture" as used herein means a mixture of flowable, particulate solids, such as powders, granules, crystals, flakes, etc. "Flowable" as used herein means that under light stress particles of the mixture will move relative to adjacent particles. (The particles of such mixtures may have a moderate tendency to adhere to adjacent particles. For example, some commercial capsule filling machines lightly compress the particulate mixture being filled into capsule shells such that a "plug" of the particulate mixture is formed. Such a plug of material may have sufficient cohesiveness to remain intact with gentle handling outside the capsule shell. However, such a plug of material can be easily broken apart under light pressure, and such material is considered to be flowable herein.) The particulate mixture comprises an active drug ingredient, polyvinylpyrrolidone, and carboxyvinylpolymer. Preferred pharmaceutical capsules of the present invention also contain other pharmaceutical carriers which aid in the preparation of the capsules. The necessary and optional ingredients are described in detail below.

When a sustained release pharmaceutical capsule of the present invention is administered orally to a patient, the patient swallows the capsule so that it reaches the stomach intact. The capsule shell is generally of such material such that it dissolves in the acidic stomach gastric juice. Upon dissolution of the capsule shell, the gastric juice wets the particulate mixture that was within the capsule shell. Instead of the particles dispersing in the gastric juice, the wetting of the outer thickness of the particulate mixture results in the formation of a cohesive mass which does not disperse or substantially swell but remains intact in the acid stomach medium.

Upon passing from the acidic stomach medium to the more alkaline environs of the intestines, the cohesive mass softens and slowly erodes. In this way, a sustained release of the active drug ingredient is made available in the intestines for providing its activity there or for absorption into the systemic system.

Polyvinylpyrrolidone

In the sustained release pharmaceutical capsules of the present invention, it has been found that polyvinylpyrrolidone is a necessary ingredient to achieve sustained release of the active drug ingredient involved. As used herein, "polyvinylpyrrolidone" or "PVP" is poly[1-(2-oxo-1-pyrrolidinyl)ethylene]:

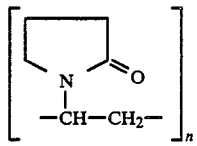

(See "7594. Povidone", The Merck Index, tenth ed. (1983), p. 1106.)

Polyvinylpyrrolidone useful in the present invention is produced commercially as a series of products having mean molecular weights ranging from about 5,000 to about 1,000,000. Polyvinylpyrrolidone preferably used in the present invention has a mean molecular weight of from about 7,000 to about 700,000.

The primary purpose of the polyvinylpyrrolidone in the sustained release pharmaceutical capsules of the present invention is to provide for the formation of the cohesive mass rapidly upon being wetted by gastrointestinal juice, when the capsule shell is permeated by the juice. Without the presence of polyvinylpyrrolidone in the particulate mixture, either a cohesive mass does not form, or any mass that does form does not have sufficient structure to provide the desired sustained release function. If sufficient polyvinylpyrrolidone is present in the particulate mixture to initially form a stable cohesive mass, a greater percentage of polyvinylpyrrolidone in the particulate mixture has little or no effect on the duration of sustained release of the active drug ingredient from the cohesive mass.

The particulate mixture of the sustained release pharmaceutical capsules of the present invention comprises from about 5% to about 96% of polyvinylpyrrolidone, preferably from about 10% to about 80% of polyvinylpyrrolidone, more preferably from about 15% to about 70% of polyvinylpyrrolidone, more preferably still from about 20% to about 60% of polyvinylpyrrolidone. The particle size of the polyvinylpyrrolidone in the particulate mixture preferably is such that 100 percent of particles which will pass through a 60 mesh sieve (U.S. Standard Screen).

Carboxyvinylpolymer

Carboxyvinylpolymer is another necessary ingredient in order to achieve the sustained release pharmaceutical capsules of the present invention. The term "carboxyvinylpolymer" as used herein describes a family of compounds disclosed and claimed in U.S. Pat. No. 2,798,053 issued to Brown on July 2, 1957.

A carboxyvinylpolymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least 4 carbon atoms to which are attached at least 3 hydroxyl groups, the polyether containing more than one alkenyl group per molecule. Other monoolefinic monomeric materials may be present in the monomeric mixture if desired, even in predominant proportion. Carboxyvinylpolymers are substantially insoluble in liquid, volatile organic hydrocarbons and are dimensionally stable on exposure to air.

Preferred polyhydric alcohols used to produce carboxyvinylpolymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least 2 allyl ether groups per polyol molecule. When the polyol is sucrose, it is preferred that the sucrose have at least about 5 allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing carboxyvinylpolymers used herein include monomeric, polymerizable, alpha-beta monoolefinically unsaturated lower aliphatic carboxyic acids; more preferred are monomeric monoolefinic acrylic acids of the structure:

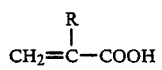

where R is a substituent selected from the group consisting of hydrogen and lower alkyl groups; most preferred is acrylic acid.

Preferred carboxyvinylpolymers used in formulations of the present invention have a molecular weight of at least about 750,000; more preferred are carboxyvinylpolymers having a molecular weight of at least about 1,250,000; most preferred are carboxyvinylpolymers having a molecular weight of from about 2,500,000 to about 4,500,000.

Various carboxyvinylpolymers are commercially available from B. F. Goodrich Company, Cleveland, Ohio, under the tradename Carbopol. Carboxyvinylpolymers preferred for use in the sustained pharmaceutical capsules of the present invention include Carbopol 940 having a molecular weight of about 4,000,000 and Carbopol 941 having a molecular weight of about 1,250,000. Highly preferred Carbopol 934 is a very slightly cross-linked carboxyvinylpolymer having a molecular weight of about 3,000,000. It has been described as a high molecular weight polyacrylic acid cross-linked with about 1% of polyallyl sucrose having an average of about 5.8 allyl groups for each molecule of sucrose.

The primary function of the carboxyvinylpolymer in the sustained release pharmaceutical capsules of the present invention is to control the duration of the sustained release of the active drug ingredient. As the percentage of carboxyvinylpolymer in the particulate mixture is increased, the duration of sustained release of the active drug ingredient increases; therefore, the percentage of carboxyvinylpolymer is adjusted to achieve the desired sustained release rate of the active drug ingredient.

The particulate mixture of the sustained release pharmaceutical capsules of the present invention comprise from about 4% to about 40% of carboxyvinylpolymer, preferably from about 5% to about 25% of carboxyvinylpolymer, more preferably from about 6% to about 15% of carboxyvinylpolymer, more preferably still from about 7% to about 10% of carboxyvinylpolymer. The particle size of the carboxyvinylpolymer in the particulate mixture preferably is such that 100 percent of particles will pass through a 60 mesh sieve (U.S. Standard Screen). (Due to adherence of carboxyvinylpolymer particles to one another, force may be required to pass the carboxyvinylpolymer particles through such sieve.)

Active Drug Ingredient

The sustained release pharmaceutical capsules of the present invention contain, in the particulate mixture, a safe and effective amount of an active drug ingredient which is a weak acid, neutral, or a weak base. The term "active drug ingredient" as used herein describes any pharmaceutical substance expected to provide a therapeutic action when the capsule is administered to a patient. As used herein "weak acid" means an acid having a dissociation constant of less than about $10^{-2}$; preferably such weak acid active drug ingredient has a dissociation constant of less than about $10^{-4}$. As used herein, "weak base" means a base having a dissociation constant of less than about $10^{-2}$; preferably such weak base active drug ingredient has a dissociation constant of less than about $10^{-4}$.

As used herein, "safe and effective amount" refers to the quantity of an active ingredient which is sufficient to yield a desired therapeutic response without undue adverse effects (such as toxicity, irritation, or allergic response), commensurate with a reasonable benefit/risk ratio. The specific safe and effective amount will vary with such factors as the particular condition being treated, the physical condition of the patient, the nature of concurrent therapy (if any), and the specifi active drug ingredient and formulation employed.

A wide variety of active drug ingredients which are orally administered may be incorporated in the sustained release capsules of the present invention. These include, but are not limited to, the following examples: sulfonamides, such as sulfadiazine, sulfamethoxazole, sulfamerazine; penicillins, such as benzyl penicillin, ampicillin, cloxacillin; tetracyclines, such as tetracycline, chlortetracycline, demeclocycline, methacycline; nitrofurans, such as nitrofurantoin and furazolidone; nalidixic acid; antifungals, such as griseofulvin and flucytosine; antiarrhythmics, such as procanamide, propranolol, verapamil; diuretics, such as acetazolamide, chlorothiazide, furosamide; hypotensive agents, such as hydralazine, clonidine, prozosin; antiasthmatic agents, such as theophylline; antihistamines, such as chlorpheniramine, methapyriline, diphenhydramine; glucocortizoids, such as cortisone and methyl prednisolone; hypoglycemic agents such as tolbutamide; diphosphonates, such as etidronate; sympathetic stimulants, such as levodopa; sympathominetic amines, such as ephedrine, phenylephrine, phenenyl propanolamine; muscle relaxants, such as dantrolene and carisoprodol; analgesics and anti-inflammatory agents, such as aspirin, acetaminophen, phenylbutazone, indomethacin and ibuprofen; expectorants and antitussives, such as guaifenesin and dextromethorphan; sedatives, such as chloral hydrate, meprobamate, diazepam; antitubercular agents, such as isoniazid; anticonvulsants, such as phenobarbital, phenytoin; tranquilizers, such as chlorpromazine haloperidol; stimulants, such as imipramine.

Depending on its solubility in the gastrointestinal juice in contact with the cohesive mass and molecular weight, some of the active drug ingredient may diffuse from the cohesive mass after it forms in the gastrointestinal tract. weak base active drug ingredients will generally diffuse more readily into the acidic gastric juice of the stomach, while weak acid active drug ingredients will generally diffuse more readily into the basic intestinal juices. For many active drug ingredients, especially those only sparingly soluble in one or more of the gastrointestinal juice(s), very little active drug ingredient diffuses from the cohesive mass in that part of the gastrointestinal tract where such juice(s) are present. Active drug ingredients for which little or no diffusion from the cohesive mass occurs in the stomach are preferred for the sustained release pharmaceutical capsules of the present invention.

For the sustained release pharmaceutical capsules of the present invention, the particulate mixture comprises from about 0.01% to about 90% of an active drug ingredient, preferably from about 1% to about 70% of an active drug ingredient, more preferably from about 10% to about 60% of an active drug ingredient.

It is important that the active drug ingredient, the polyvinylpyrrolidone and the carboxyvinylpolymer be substantially uniformly mixed in the particulate mixture of the sustained release pharmaceutical capsules of the present invention. In order to achieve such a substantially uniform mixture, it is preferred that the active drug ingredient have a particle size range similar to that of the polyvinylpyrrolidone and carboxyvinylpolymer.

The particle size of the active drug ingredient preferably is such that 100 percent of the particles will pass through a 60 mesh sieve (U.S. Standard Screen).

Optional Ingredients

For the sustained release pharmaceutical capsules of the present invention, necessary ingredients are the active drug ingredient, polyvinylpyrrolidone, and carboxyvinylpolymer as described hereinabove. Other pharmaceutical carriers may be added to provide capsules having the desired characteristics or as production acids. By "pharmaceutical carrier" as used herein, is meant one or more compatible solid filler diluents or solid or liquid substances added to aid in the production of the capsules, such as lubricants to reduce friction and glidants to improve flow of the particulate mixtures. By "compatible" as used herein, is meant that the components are capable of being comingled without interacting in a manner which would substantially decrease the pharmaceutical efficacy of the capsules under ordinary use situations.

Some examples of substances which can serve as pharmaceutical carriers are sugars, such as lactose, glucose and sucrose; starches, such as corn starch and potato starch; cellulose and its derivatives, such as sodium carboxymethylcellulose, ethylcellulose, cellulose acetate; powdered tragacanth; malt; gelatin; talc; stearic acid; magnesium stearate; zinc stearate; calcium sulphate; silicon dioxide; vegetable oils, such as peanut oil, cottonseed oil, sesame oil, olive oil, corn oil and oil of theobroma; polyols, such as propylene glycol, glycerine, sorbitol, mannitol, and polyethylene glycol; agar; and alginic acid; as well as other non-toxic compatible substances used in pharmaceutical formulations. Wetting agents such as sodium laural sulphate, as well as coloring agents, lubricants, excipients, stabilizers, antioxidants, and preservatives, can also be present.

Capsule Shells

The sustained release pharmaceutical capsules of the present invention comprise a particulate mixture in a capsule shell which is soluble in a gastrointestinal juice. The preferred capsule shells used for capsules of the present invention are hard gelatin capsules. Hard gelatin capsules are soluble in gastric juice. As described hereinabove, the particulate mixture of the sustained release capsules of the present invention forms a cohesive mass which is eroded very little in gastric juice. For many active drug ingredients, such cohesive mass prevents any substantial diffusion of the active drug ingredient out of the mass while it is in the gastric juice in the stomach. Therefore, unless it is necessary to prevent any of the active drug ingredient from being released in the stomach, hard gelatin capsule shells provide the needed structure to deliver the bulk of the active drug ingredient to the intestines where sustained release of the active drug ingredient occurs.

Where it is necessary to prevent any release of active drug ingredient in the stomach, a capsule shell or coated capsule shell could be used whose solubility is pH dependent such that the capsule shell or coating does not dissolve until it reaches the intestines. Further adjustment of the capsule shell material or coating material could result in dissolution of the capsule shell later in the small intestine, or even in the colon, if it is desired to begin the sustained release action of the capsules in those regions of the gastrointestinal tract.

Process for Producing Sustained Release Capsules

A preferred process for producing the sustained release pharmaceutical capsules of the present invention comprises the steps of: (1) preparing the particulate mixture, and (2) filling the particulate mixture into a capsule shell. The active drug ingredient, polyvinylpyrrolidone, and carboxyvinylpolymer raw materials for producing the sustained release pharmaceutical capsules are each preferably obtained in solid, particulate form, either as granules or powders. These separate raw materials are preferably powders.

The active drug ingredient, polyvinylpyrrolidone, carboxyvinylpolymer, and any pharmaceutical carrier powder components are preferably dry blended until the particulate mixture is substantially uniform in composition.

For a pharmaceutical carrier or active drug ingredient which is to be incorporated in the particulate mixture as a liquid, such liquid may be incorporated by spraying or other addition means and blending the particulate mixture until the liquid is uniformly dispersed therein. Although some liquid may be thus added to the particulate mixture, it retains its flowable, particulate form.

The particulate mixture is then filled into the capsule shells, preferably using standard pharmaceutical capsule filling techniques. The formation of the cohesive mass necessary to achieve the sustained release of the active drug ingredient occurs only after the capsule shell dissolves in the gastrointestinal tract and the gastrointestinal juice wets the particulate mixture that was within the capsule shell.

Combination Sustained Release/Rapid Release Capsules

For most active drug ingredients, there is a minimum therapeutic concentration of the active drug that must be reached in a target tissue, if the desired therapeutic effect is to occur. A sustained release pharmaceutical dosage form generally makes an active drug ingredient available for absorption and/or use in the patient's body a little bit at a time over an extended period of time. If the active drug is metabolized or otherwise eliminated by the patient's body, it may be a very long time or never that the drug ingredient reaches such minimum therapeutic concentration in the target tissue(s) of the patient. In order to overcome this, it is often necessary to provide an initial rapid release dose of the active drug ingredient to rapidly achieve such minimum therapeutic concentration. Once such minimum therapeutic concentration is surpassed in the target tissue(s), the sustained release dosage form can maintain it by delivering the active drug ingredient in sufficient quantities to compensate for the amount of active drug which is metabolized or otherwise eliminated from the target tissue(s).

Another aspect of the present invention is a combination sustained release/rapid release pharmaceutical capsule which can provide both the rapid release of the active drug ingredient in ordr to quickly achieve the minimum therapeutic concentration of the active drug in the target tissue(s) of a patient, along with a sustained release dose of the active drug ingredient in order to retain such minimum therapeutic concentration or greater in the target tissue(s) over an extended period. The rapid release portion of this combination sustained release/rapid release capsule of the present invention can be achieved by including a separate intact dosage unit form for the rapid release portion in the capsule shell, e.g. a pellet, tablet, small capsule, etc.

The combined sustained release/rapid release pharmaceutical capsules for oral administration of the present invention preferably comprise, in a capsule shell which is soluble in a gastrointestinal juice: (1) a first layer of a first particulate mixture, said first particulate mixture being the same as the sustained release particulate mixture described hereinabove; and (2) a second layer of a second particulate mixture preferably comprising the same active drug 16 ingredient as in said first particulate mixture. The first layer of the combination sustained release/rapid release pharmaceutical capsules provides a sustained release of the active drug ingredient in the same manner as for the sustained release pharmaceutical capsules described hereinabove. The second layer provides a rapid release portion of the active drug ingredient by providing a second particulate mixture comprising the active drug ingredient, the second particulate mixture being formulated such that it rapidly disperses upon dissolution of the capsule shell in the gastrointestinal tract. The second mixture is preferably a mixture of the active drug ingredient and one or more pharmaceutical carriers formulated to achieve such rapid dispersion in the gastrointestinal tract.

The combined sustained release/rapid release capsules of the present invention can provide, in a dosage unit form, a rapid release of one active drug ingredient and a sustained release of a second active drug ingredient, if desired, by incorporating different active drug ingredients in the first and second particulate mixtures described hereinabove.

The capsule shell of the combination sustained release/rapid release capsules of the present invention is preferably made such that it dissolves in the portion of the gastrointestinal tract where the active drug ingredient of the rapid release (second particulate) mixture is readily utilized, absorbed, or otherwise transported to the target tissue(s) where its activity is utilized.

Process for Producing the Combination Sustained Release/Rapid Release Capsules

The combination sustained release/rapid release pharmaceutical capsules are preferably produced by a process comprising the steps of: (1) preparing a first particulate mixture, said first particulate mixture being the same as for the sustained release pharmaceutical capsules described hereinabove; (2) preparing a second particulate mixture, preferably comprising the same active drug ingredient as in said first particulate mixture; and (3) filling, into a capsule shell, a first layer of said first particulate mixture, and a second layer of said second particulate mixture. The combination sustained release/rapid release pharmaceutical capsules of the pesent invention can be easily and inexpensively produced using standard pharmaceutical industry mixing and capsule-filling equipment.

Two separate particulate mixtures are produced. The first particulate mixture is the same as for the sustained release pharmaceutical capsules described hereinabove. The second particulate mixture comprises an active drug ingredient, and preferably any pharmaceutical carriers as described hereinbefore needed to provide a second particulate mixture which can be readily filled into capsules using a capsule-filling machine, and such that the second particulate mixture will rapidly disperse in the gastrointestinal juice when the capsule shell dissolves. The formulation of such second particulate mixtures is well within the purview of a person skilled in the art of formulating pharmaceutical capsule compositions.

The sustained release and rapid release particulate mixtures are then filled into a capsule shell in separate layers, preferably using standard pharmaceutical capsule-filling machines. The order in which the sustained release and rapid release mixtures are filled into the capsule shell is not important. For the combination sustained release/rapid release pharmaceutical capsules, it is preferred that there be a single layer of sustained release (first particulate) mixture and a single layer of rapid relese (second particulate) mixture. However, more than one layer of either or both of the particulate mixtures could be included in such capsules.

The following nonlimiting examples describe sustained release pharmaceutical capsules and combination sustained release/rapid release pharmaceutical capsules of the present invention and processes for producing them.

EXAMPLE 1

Sustained release capsules of the present invention are made according to the following formulation:

| Ingredient | Weight Per Batch (g) | Weight Per Capsule (mg) | Weight Percent |
|---|---|---|---|
| Nitrofurantoin monohydrate | 15.00 | 150.0 | 42.4 |
| Carbopol 934P | 1.77 | 17.7 | 5.0 |
| PVP C-15 | 18.10 | 181.0 | 51.1 |
| Talc | 0.35 | 3.5 | 1.0 |
| Zinc Stearate | 0.18 | 1.8 | 0.5 |
| Total | 35.40 | 354.0 | 100.0 |

The Carbopol 934P (pharmaceutical grade of Carbopol 934, B. F. Goodrich Chemical Company, Cleveland, Ohio), PVP C-15 (mean molecular weight of about 8,000, GAF Corporation, Wayne, N.J.), talc, and zinc stearate are combined in a mortar and triturated well. The nitrofurantoin monohydrate (Norwich Eaton Pharmaceuticals, Inc., Norwich, N.Y.) is added to this mixture in the mortar and triturated well until a substantially uniform particulate mixture is achieved. The resulting particulate mixture is hand filled into size 1 hard gelatin capsule shells.

Samples of the capsules are subjected to disslution testing using USP Apparatus 2 (U.S. Pharmacopeia XXI, 1985, pp. 1243-4) separately in simulated gastric fluid (SGF), pH 1.2 (U.S. Pharmacopeia XXI, 1985, p. 1424), and simulated intestinal fluid (SIF), pH 7.5 (U.S. Pharmacopeia XXI, 1985, p. 1424), as dissolution media, paddle speed 100 rpm, temperature 37° C. Samples are taken from the dissolution medium at time 0 and at each ½ hour interval and are assayed for active drug content until 90% of the active drug is found to be in solution. The simulated gastric and intestinal fluids are the same as provided for in the USP except that they do not contain the enzymes. Capsules are weighted down in the dissolution flask by coiling a wire around them.

The nitrofurantoin is assayed in the dissolution media by monitoring samples of the medium spectrophotometrically at 367 nm for SGF and at 383 nm for SIF and comparing with calibrated solutions of known nitrofurantoin content.

The sustained release performance of the capsules is demonstrated by the time required for 50% ($T_{50}$) and 90% ($T_{90}$) of the active drug to be detected in the dissolution medium. For the capsules produced according to this Example 1, $T_{50}$ and $T_{90}$ were not determined in SGF since only 8% of the nitrofurantoin was detected in the dissolution medium after 2 hours; in SIF, $T_{50}=1.5$ hr and $T_{90}=4.0$ hr.

EXAMPLE 2

Sustained release capsules of the present invention are made according to the following formulation:

| Ingredient | Weight Per Batch (g) | Weight Per Capsule (mg) | Weight Percent |
|---|---|---|---|
| Nitrofurantoin anhydrous acid | 15.00 | 150.0 | 42.4 |
| Carbopol 934P | 2.66 | 26.6 | 7.5 |
| PVP K-90 | 17.21 | 172.1 | 48.6 |
| Talc | 0.35 | 3.5 | 1.0 |
| Zinc Stearate | 0.18 | 1.8 | 0.5 |
| Total | 35.40 | 354.0 | 100.0 |

A particulate mixture of nitrofurantoin (anhydrous acid, Norwich Eaton Pharmaceuticals, Inc., Norwich, N.Y.) PVP K-90 (mean molecular weight of about 630,000, GAF Corporation, Wayne, N.J.) and the other ingredients above are prepared and capsules are produced and tested according to the methods described in Example 1. The resulting capsules have $T_{50}=2.0$ hr and $T_{90}=6.0$ hr in SIF; only 8% of the nitrofurantoin is detected in SCF medium after 2 hours.

EXAMPLE 3

Sustained release capsules of the present invention are made according to the following formulation:

| Ingredient | Weight Per Batch (g) | Weight Per Capsule (mg) | Weight Percent |
|---|---|---|---|
| Nitrofurantoin monohydrate | 2152 | 215.2 | 43.5 |
| Carbopol 941 | 495 | 49.5 | 10.0 |
| PVP K-29/32 | 1238.7 | 123.87 | 25.0 |
| Talc | 49.5 | 4.95 | 1.0 |
| Cabosil | 49.5 | 4.95 | 1.0 |
| Dipac | 866.3 | 86.63 | 17.5 |
| Magnesium Stearate | 99 | 9.9 | 2.0 |
| Total | 4950 | 495.0 | 100.0 |

The nitrofurantoin monohydrate, Carbopol 941 (B. F. Goodrich Chemical Co., Cleveland, Ohio), PVP K-29/32 (mean molecular weight of about 40,000, GAF Corporation, Wayne, N.J.), Cabosil (colloidal silicon dioxide, Commercial Chemicals, Inc., Buffalo, N.Y.), and talc are blended in a V-blender (Patterson-Kelly Co., East Stroudsburg, Pa.) for 10 minutes. The mixture is then sifted through a 60 mesh sieve (U.S. Standard Screen) using a Stokes Oscillating Granulator (Model 900-43-6, Sharples-Stokes Division, Pennwalt Corp., Warminster, Pa.) in order to eliminate any agglomerates or lumps of material; lumps are broken up and all material is forced through the screen. The mixture is further blended in the V-blender with sequential addition of the Dipac (compressible sugar, Amstar Corp., Brooklyn, N.Y.) and magnesium stearate until a substantially uniform particulate mixture is obtained.

Capsules are produced using a commercial capsule filling machine (Harro Hofliger Model KFM/3, M. O. Industries, East Hanover, N.J.) by filling 495 mg of the particulate mixture into size 0 hard gelatin capsules. The sustained release properties of the capsules are tested according to the method in Example 1; $T_{50}=3.0$ hr and $T_{90}=7.0$ hr in SIF; only 6% of the nitrofurantoin is detected in SGF after 2 hours.

EXAMPLE 4

Sustained release capsules of the present invention are made according to the following formulation:

| Ingredient | Weight Per Batch (g) | Weight Per Capsule (mg) | Weight Percent |
|---|---|---|---|
| Nitrofurantoin monohydrate | 15.00 | 150.0 | 42.4 |
| Carbopol 934P | 5.31 | 53.1 | 15.0 |
| PVP C-15 | 14.56 | 145.6 | 41.1 |
| Talc | 0.35 | 3.5 | 1.0 |
| Zinc Stearate | 0.18 | 1.8 | 0.5 |
| Total | 35.40 | 354.0 | 100.0 |

A particulate mixture of sodium nitrofurantoin (Norwich Eaton Pharmaceuticals, Inc., Norwich, N.Y.) and the other ingredients above are prepared and capsules are prepared and tested according to the methods described in Example 1. The resulting capsules have $T_{50}=4.0$ hr and $T_{90}=8.0$ hr in SIF; only 5% of the nitrofurantoin is detected in SGF after 2 hours.

EXAMPLE 5

Sustained release capsules of the present invention are made according to the following formulation:

| Ingredient | Weight Per Batch (g) | Weight Per Capsule (mg) | Weight Percent |
|---|---|---|---|
| Nitrofurantoin monohydrate | 15.00 | 150.0 | 42.4 |
| Carbopol 934P | 8.85 | 88.5 | 25.0 |
| PVP C-15 | 11.02 | 110.2 | 31.1 |
| Talc | 0.35 | 3.5 | 1.0 |
| Zinc Stearate | 0.18 | 1.8 | 0.5 |
| Total | 35.4 | 354.0 | 100.0 |

A particulate mixture of the above ingredients is prepared and capsules are prepared and tested according to the methods described in Example 1. The resulting capsules have $T_{50}=5.5$ hr and $T_{90}=11.0$ hr in SIF; only 3% of the nitrofurantoin is detected in SGF after 2 hours.

EXAMPLE 6

Sustained release capsules of the present invention are made according to the following formulation:

| Ingredient | Weight Per Batch (g) | Weight per Capsule (mg) | Weight Percent |
|---|---|---|---|
| Theophylline | 15.00 | 150.0 | 42.4 |
| Carbopol 934P | 2.66 | 26.6 | 7.5 |
| PVP C-15 | 17.21 | 172.1 | 48.6 |
| Talc | 0.35 | 3.5 | 1.0 |
| Zinc Stearate | 0.18 | 1.8 | 0.5 |
| Total | 35.40 | 354.0 | 100.0 |

A particulate mixture of theophylline (MWM Chemical Corp., New York, N.Y.), and the other ingredients above, is prepared and capsules are prepared and tested according to the methods described in Example 1, except that the method for assaying Theophylline uses a wavelength of 270 nm in SGF and 272 nm in SIF. The resulting capsules have $T_{50}=1$ hr and $T_{90}=4$ hr in SGF, and $T_{50}=2.5$ hr and $T_{90}=5$ hr in SIF.

EXAMPLE 7

Sustained release capsules of the present invention are made according to the following formulation:

| Ingredient | Weight Per Batch (g) | Weight Per Capsule (mg) | Weight Percent |
|---|---|---|---|
| Guaifenesin | 15.00 | 150.0 | 42.4 |
| Carbopol 934P | 2.66 | 26.6 | 7.5 |
| PVP C-15 | 17.21 | 172.1 | 48.6 |
| Talc | 0.35 | 3.5 | 1.0 |
| Zinc Stearate | 0.18 | 1.8 | 0.5 |
| Total | 35.40 | 354.0 | 100.0 |

A particulate mixture of Guaifenesin (Rhone-Poulenc Corp., Monmouth Junction, N.J.), and the other ingredients above, is prepared and capsules are prepared and tested according to the methods described in Example 1, except that the method for assaying Guaifenesin uses a wavelength of 273 nm in both SGF and SIF. The resulting capsules have $T_{50}=1$ hr and $T_{90}=4\frac{1}{2}$ hr in SGF and $T_{50}=3.5$ hr and $T_{90}=7$ hr in SIF.

EXAMPLE 8

Combination sustained release/rapid release capsules of the present invention are made according to the following formulation:

| | Sustained Release Mixture | | |
|---|---|---|---|
| Ingredient | Weight Per Batch (g) | Weight Per Capsule (mg) | Weight Percent |
| Nitrofurantoin monohydrate | 1614 | 161.4 | 45.6 |
| Carbopol 934P | 283.2 | 28.32 | 8.0 |
| PVP C-15 | 881.7 | 88.17 | 24.9 |
| Talc | 35.4 | 3.54 | 1.0 |
| Cabosil | 35.4 | 3.54 | 1.0 |
| Dipac | 619.5 | 61.95 | 17.5 |
| Magnesium Stearate | 70.8 | 7.08 | 2.0 |
| Total | 3540 | 354.0 | 100.0 |

The sustained release particulate mixture is prepared from the above ingredients according to the method described in Example 3.

| | Rapid Release Mixture | | |
|---|---|---|---|
| Ingredient | Weight Per Batch (g) | Weight Per Capsule (mg) | Weight Percent |
| Macrodantin ® | 500. | 50.0 | 15.4 |
| Talc | 230. | 23.0 | 7.1 |
| Starch | 380. | 38.0 | 11.7 |
| Lactose, hydrous | 2140. | 214.0 | 65.8 |
| Total | 3250. | 325.0 | 100.0 |

The rapid release particulate mixture is prepared by adding the Macrodantin ® (Norwich Eaton Pharmaceuticals, Inc., Norwich, N.Y.) and the other above ingredients to a V-blender and mixing for 10 minutes.

Capsules are prepared by first filling 325 mg of the rapid release particulate mixture as a first layer into size 0 hard gelatin capsule shells using the capsule filling machine described in Example 3. After such first layer is filled into the capsule shells, the resulting partially filled capsules are again fed into the capsule filling machine and 354 mg of the sustained release particulate mixture is filled into each capsule shell as a second layer on top of the rapid relase particulate mixture.

The capsules are tested according to the methods described in Example 1 except that ony one test is performed in which SGF is the dissolution medium for the first hour of the test and then SIF is the dissolution medium for the remainder of the test. After the one hour in SGF, 15% of the total nitrofurantoin dose from the capsule is in solution; $T_{90}=6$ hr.

While particular embodiments of the present invention have been described, it will be obvious to those skilled in the art that various changes and modifications of the pharmaceutical capsules of the present invention and the processes for producing them can be made without departing from the spirit and scope of the invention. It is intended to cover, in the appended claims, all such modifications that are within the scope of this invention.

What is claimed is:

1. A sustained release pharmaceutical capsule for oral administration comprising a particulate mixture, in a capsule shell which is soluble in a gastrointestinal juice, said particulate mixture comprising:
   (a) from about 0.01% to about 90% of an active drug ingredient which is a weak acid, neutral, or a weak base;
   (b) from about 5% to about 96% of polyvinylpyrrolidone; and
   (c) from about 4% to about 40% of carboxyvinylpolymer; wherein said polyvinylpyrrolidone and said carboxyvinylpolymer occur substantially entirely in separate particles of said particulate mixture.

2. The capsule of claim 1 wherein said particulate mixture comprises from about 10% to about 70% of polyvinylpyrrolidone.

3. The capsule of claim 1 wherein said particulate mixture comprises from about 15% to about 60% of polyvinylpyrrolidone.

4. The capsule of claim 2 wherein said particulate mixture comprises from about 5% to about 25% of carboxyvinylpolymer.

5. The capsule of claim 3 wherein said particulate mixture comprises from about 10% to about 70% of said active drug ingredient and from about 5% to about 15% of carboxyvinylpolymer.

6. The capsule of claim 2 wherein said particulate mixture comprises from about 10% to about 70% of said active drug ingredient and from about 7% to about 10% of carboxyvinylpolymer.

7. The capsule of claim 4 wherein said carboxyvinylpolymer has a molecular weight of at least about 1,250,000, and said capsule shell is a hard gelatin capsule shell which is soluble in gastric juice.

8. The capsule of claim 5 wherein said carboxyvinylpolymer has a molecular weight of about 3,000,000 and is a polyacrylic acid cross-linked with about 1% of polyallyl sucrose having an average of about 5.8 allyl groups for each molecule of sucrose.

9. The capsule of claim 6 wherein said carboxyvinylpolymer has a molecular weight of about 3,000,000 and is a polyacrylic acid cross-linked with about 1% of polyallyl sucrose having an average of about 5.8 allyl groups for each molecule of sucrose.

10. The capsule of claim 8 wherein said polyvinylpyrrolidone has a molecular weight of from about 7,000 to about 700,000.

11. A process for producing a sustained release pharmaceutical capsule for oral administration comprising the steps of:
  (1) preparing a particulate mixture, said particulate mixture comprising:
    (a) from about 0.01% to about 90% of an active drug ingredient which is a weak acid, neutral, or a weak base;
    (b) from about 5% to about 96% of polyvinylpyrrolidone; and
    (c) from about 4% to about 40% of carboxyvinylpolymer; wherein said polyvinylpyrrolidone and said carboxyvinylpolymer occur substantially entirely in separate particles of said particulate mixture.
  (2) filling said particulate mixture into a capsule shell which is soluble in a gastrointestinal juice.

12. The process of claim 11 wherein said particulate mixture comprises from about 10% to about 70% of said active drug ingredient, from about 10% to about 70% of polyvinylpyrrolidone, and from about 5% to about 15% of carboxyvinylpolymer.

13. The process of claim 12 wherein said carboxyvinylpolymer has a molecular weight of at least about 1,250,000, and said capsule shell is a hard gelatin capsule shell which is soluble in gastric juice.

14. The process of claim 11 wherein said particulate mixture comprises from about 10% to about 70% of said active drug ingredient, from about 10% to about 70% of polyvinylpyrroline having a molecular weight of from about 7,000 to about 700,000, and from about 7% to about 10% of carboxyvinylpolymer having a molecular weight of about 3,000,000, said carboxyvinylpolymer being a polyacrylic acid cross-linked with about 1% of polyallyl sucrose having an average of about 5.8 allyl groups for each molecule of sucrose.

* * * * *